(12) United States Patent
Shen et al.

(10) Patent No.: US 8,536,361 B2
(45) Date of Patent: Sep. 17, 2013

(54) 1,4,6,10-TETRA-DOUBLE BOND PENTADEC-CARBON PHOSPHONATE, PREPARATION METHOD THEREOF, AND PREPARATION METHOD OF LYCOPENE USING THE SAME

(76) Inventors: Runpu Shen, Xinchang County (CN); Weidong Ye, Xinchang County (CN); Shiqing Pi, Xinchang County (CN); Xuejun Lao, Xinchang County (CN); Luo Liu, Xinchang County (CN); Xiaohua Song, Xinchang County (CN); Chunlei Wu, Xinchang County (CN); Zhigang Wu, Xinchang County (CN)

( * ) Notice: Subject to any disclaimer, the term of this patent is extended or adjusted under 35 U.S.C. 154(b) by 0 days.

(21) Appl. No.: 13/576,659

(22) PCT Filed: Jan. 30, 2011

(86) PCT No.: PCT/CN2011/000157
§ 371 (c)(1),
(2), (4) Date: Aug. 2, 2012

(87) PCT Pub. No.: WO2011/095052
PCT Pub. Date: Aug. 11, 2011

(65) Prior Publication Data
US 2012/0310002 A1    Dec. 6, 2012

(30) Foreign Application Priority Data

Feb. 2, 2010 (CN) .......................... 2010 1 0104281

(51) Int. Cl.
*C07F 9/142* (2006.01)
(52) U.S. Cl.
USPC .............................................. 558/87; 558/70
(58) Field of Classification Search
USPC ..................................................... 558/87, 70
See application file for complete search history.

(56) References Cited

FOREIGN PATENT DOCUMENTS

CN    101824051    *    9/2010

* cited by examiner

*Primary Examiner* — Wu-Cheng Winston Shen
*Assistant Examiner* — Karen Cheng
(74) *Attorney, Agent, or Firm* — Ash Tankha; Lipton, Weinberger & Husick

(57) ABSTRACT

1,4,6,10-tetra-double bond pentadec-carbon phosphonate of formula (4), and preparation method thereof are provided. The preparation method comprises: reacting a pseudo ionone of formula (2) with sulfonium salt to prepare a epoxide of formula (9), and then reacting the epoxide of formula (9) with magnesium bromide to prepare a C-14 aldehyde of formula (3); condensing the C-14 aldehyde of formula (3) with tetra-alkyl methylene diphosphonate to obtain 1,4,6,10-tetra-double bond pentadec-carbon phosphonate of formula (4). Furthermore, the preparation method of lycopene via 1,4,6,10-tetra-double bond pentadec-carbon phosphonate of formula (4) is also provided. The present method has the advantages of short route, easily obtained raw materials, and low cost.

14 Claims, No Drawings

1,4,6,10-TETRA-DOUBLE BOND PENTADEC-CARBON PHOSPHONATE, PREPARATION METHOD THEREOF, AND PREPARATION METHOD OF LYCOPENE USING THE SAME

CROSS REFERENCE TO RELATED APPLICATIONS

This application claims the benefit of the following patent applications:
1. Chinese patent application number 201010104281.7 titled "1,4,6,10-Tetra-Double Bond Pentadec-Carbon Phosphonate, Preparation Method thereof, and Preparation Method of Lycopene Using the Same", filed in the State Intellectual Property Office of the People's Republic of China on Feb. 2, 2010.
2. PCT application number PCT/CN2011/000157 titled "1,4,6,10-Tetra-Double Bond Pentadec-Carbon Phosphonate, Preparation Method thereof, and Preparation Method of Lycopene Using the Same", filed in the State Intellectual Property Office of the People's Republic of China on Jan. 30, 2011.

The specifications of the above referenced patent applications are incorporated herein by reference in their entirety.

FIELD OF THE INVENTION

The invention relates to a new intermediate 1,4,6,10-tetra-double bond pentadec-carbon phosphonate, preparation method thereof, in particular, relates to a method of preparing lycopene by using the intermediate 1,4,6,10-tetra-double bond pentadec-carbon phosphonate.

BACKGROUND OF THE INVENTION

There are approximately 600 kinds of carotenoids naturally, but only six kinds of these have so far been produced industrially such as production by Roche Corporation and BASF Corporation. Lycopene as an important product has important functions on scavenging free radical, antiageing, inhibiting tumor, treating heart attack and so on (H. Gerster, J. Am. Coll. Nutr. 1997, 16, 109; Nutr. Cancer 1995, 24.257; E. Giovannucci. et al. J. Natl. Cancer Inst. 1995, 87, 1767; Chem. Abstracts 1990, 112 91375w), and is widely used for medicines, food additives, feed additives. Roche Corporation develops a synthesis route by the Witting Reaction, wherein it uses expensive and poisonous raw materials such as tri-phenyl phosphorous (K. Meyer, et al., Helv. Chim. Acta 1992, 75.1848). Other former synthesis methods use tri-phenyl phosphorous either (P. Karrer, et al., Helv. Chim. Acta 1950, 33, 1349; B. C. L. Weedon, et al., J. Chem. Soc. 1965, 2019; K. Bernhard and H. Mayer, Pure & Appl.-them. 1991, 63, 35).

It has been reported from Publication No. WO 0031086 (2000 Jun. 2) of PCT application that Babler J. H. et al. reported a new method of synthesizing lycopene by the Wittig-Horner Reaction, wherein 3,7,11-trimethyl-2,4,6,10-dodecatetraenyl phosphonic acid diethyl ester of formula (5) as a crucial intermediate proceeds a condensation reaction with decyl di-aldehyde by catalysis of bases for preparing lycopene, the whole synthesis sequence is described as follows.

Firstly, pseudoionone (2) reacts with ethynyl anion to produce tertiary alcohol (7) (3,7,11-trimethyl-4,6,10-dodecatrien-1-yn-3-ol):

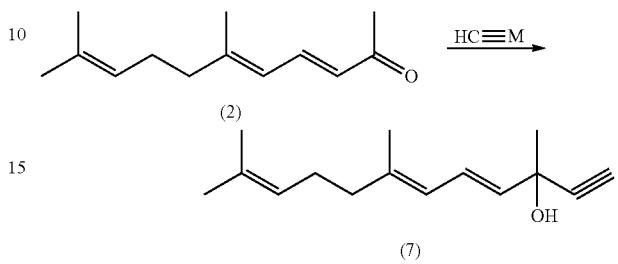

Afterwards, tertiary alcohol (7) reacts with dialkyl chlorophosphite to produce propadiene pentadecyl phosphoric acid ester (6) (3,7,11-trimethyl-1,2,4,6,10-dodecapentaenyl phosphoric acid diethyl ester).

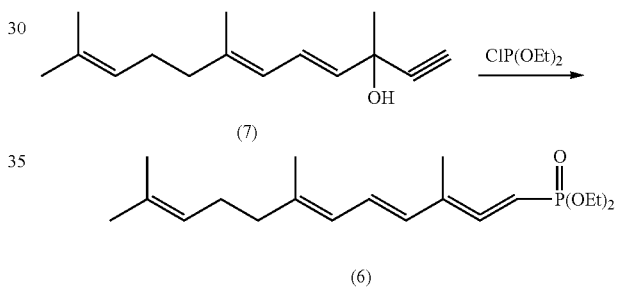

Secondly, propadiene pentadecyl phosphoric acid ester (6) is partially reduced and transformed to pentadecyl phosphoric acid ester (5) (3,7,11-trimethyl-2,4,6,10-dodecatetraenyl phosphoric acid diethyl ester):

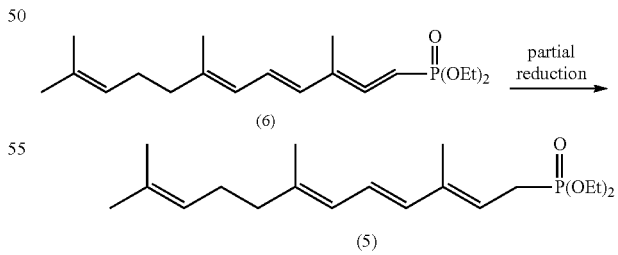

Finally, pentadecyl phosphoric acid ester (5) proceeds a condensation reaction with decanal di-aldehyde (8) (2,7-dimenthyl-2,4,6-octatriene-1,8-dial) by catalysis of bases to obtain lycopene (1).

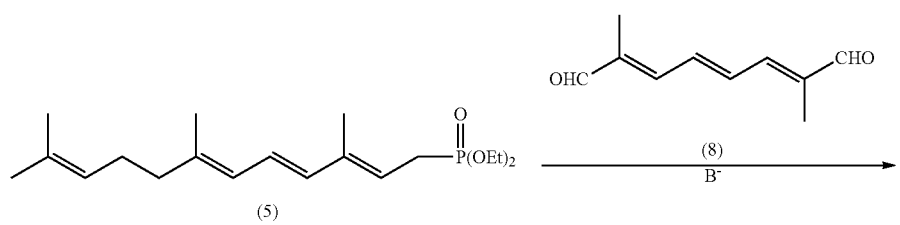
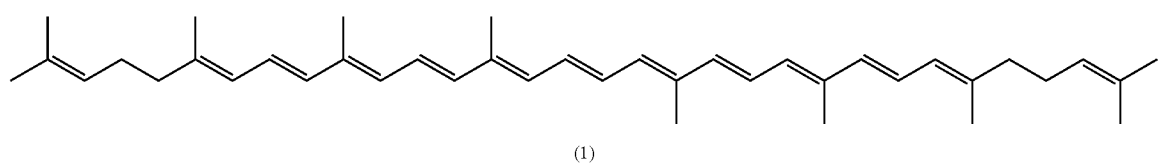

The method uses a new compound 2,4,6,10-pentadecatetraenyl phosphoric acid ester (5) as an intermediate to avoid uses of triphenyl phosphorous; and moreover uses pseudoionone as a raw material to obtain products of lycopene by reactions of four steps. The synthesis route thereof is concise, and has prominent improvement relative to former methods. However there are some problems in the method. Firstly it is difficulty for reactions of tertiary alcohol (7) with dialkyl chlorophosphite to produce propadiene pentadecyl phosphoric acid ester (6). Secondly it is hard to handle the reduction technology of propadiene pentadecyl phosphoric acid ester (6) selectively being reduced to pentadecyl phosphoric acid ester (5).

After studying features and preparation of 2,4,6,10-dodecatetraenyl phosphoric acid ester of formula (5), the inventors found that there would be a method of preparing products of structure analogue in early patents (U.S. Pat. No. 4,916,250). The process is by a condensation reaction of Wittig-Horner of C-14 aldehyde and methylene bisphosphonic acid tetraethyl ester to produce 1-enyl isomer thereof, and then to catalyze and rearrange by base to obtain 2-enyl isomer. As shown in the following reaction sequence.

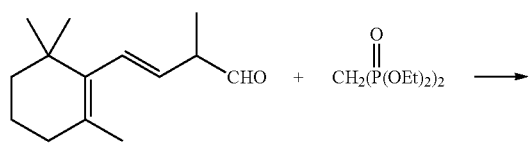

-continued

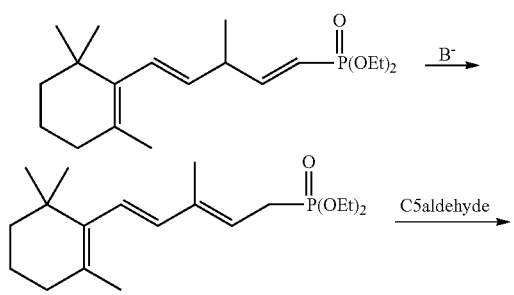

The reaction sequence is concise, operable and high yield. Consequently it would be great advantages of preparing 2,4,6,10-pentadecatetraenyl phosphoric acid ester (5) by using C-14 aldehyde as raw materials and further produce lycopene.

PCT publication No. WO 0031086 and U.S. Pat. Nos. 4,916,250, 6,727,381, 4,000,131 and 5,061,819 are hereby incorporated by reference.

The inventors of the present invention prepare 2,4,6,10-pentadecatetraenyl phosphoric acid ester by using C-14 aldehyde as raw materials and further prepare lycopene according to methods of U.S. Pat. No. 4,916,250. As shown in the following reaction sequence.

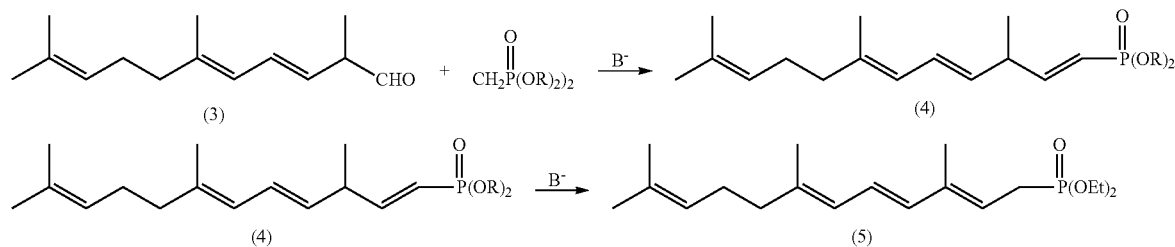

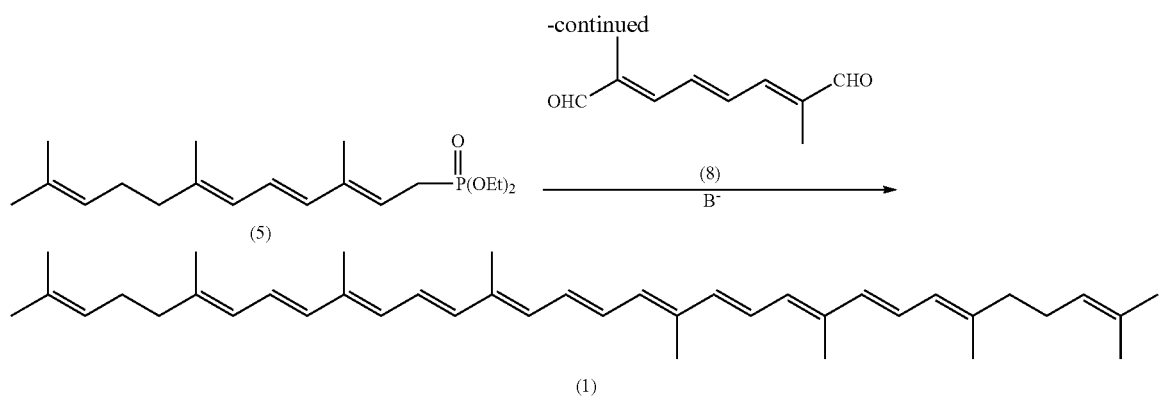

The inventors of the present invention found a group of new compounds 1,4,6,10-pentadecatetraenyl phosphonic acid ester (4) in the synthesis process may be used as a crucial intermediate in the process. Mr. Shiqing Pi and Runbo Shen et al. mentioned in an early patent (U.S. Pat. No. 6,727,381) that a compound analogous to 1-enyl pentadecyl phosphonic acid ester directly reacts with C-5 aldehyde to produce Vitamin A. As shown in the following reaction sequence.

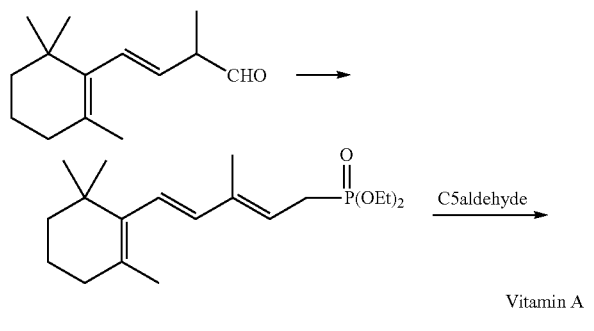

Accordingly, it would be reasonable to expect a new compound 1,4,6,10-pentadecatetraenyl phosphoric acid ester of formula (4), that is, 1,4,6,10-pentadecatetraenyl phosphoric acid ester of formula (4) directly proceeds a condensation reaction with decyl di-aldehyde of formula (8) to obtain lycopene of formula (1), but not by a rearrangement reaction from 1,4,6,10-pentadecatetraenyl phosphoric acid ester of formula (4) to 2,4,6,10-pentadecatetraenyl phosphoric acid ester of formula (5).

SUMMARY OF THE INVENTION

The first objective of the present invention is to provide 1,4,6,10-tetra-double bond pentadec-carbon phosphonate of formula (4). The 1,4,6,10-tetra-double bond pentadec-carbon phosphonate is 3,7,11-trimethyl-1,4,6,10-dodecatetraenyl phosphoric acid dialkyl ester.

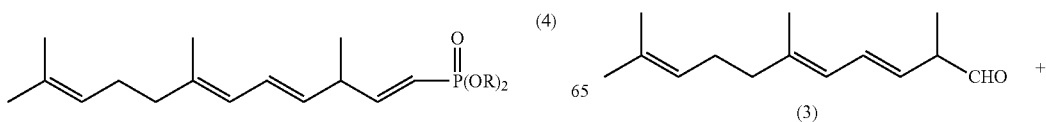

Wherein R is $C_{1-4}$ alkyl.

Preferably, the 1,4,6,10-tetra-double bond pentadec-carbon phosphonate is 3,7,11-trimethyl-1,4,6,10-dodecatetraenyl phosphoric acid di-methyl ester, 3,7,11-trimethyl-1,4,6,10-dodecatetraenyl phosphoric acid di-ethyl ester, 3,7,11-trimethyl-1,4,6,10-dodecatetraenyl phosphoric acid di-isopropyl ester.

The second objective of the present invention is to provide a method of preparing the 1,4,6,10-tetra-double bond pentadec-carbon phosphonate of formula (4), the method comprises the following steps:

Step (1): reacting a pseudo ionone of formula (2) with sulfonium salt under protection of inert gases to prepare a epoxide of formula (9), and then reacting the epoxide of formula (9) with magnesium bromide to prepare 2,6,10-trimethyl-3,5,9-undecatrienyl-1-aldehyde. Its reaction sequence is described as follows.

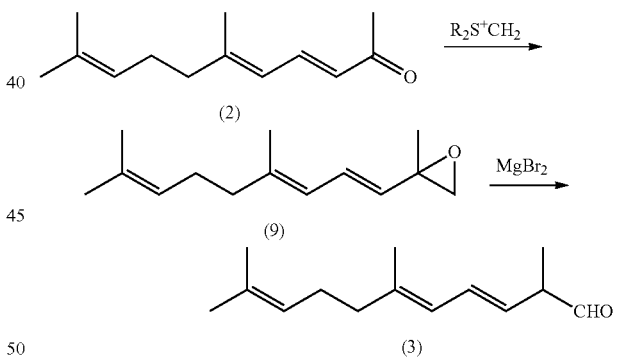

Step (2): proceeding a Wittig-Horner condensation reaction of 2,6,10-trimethyl-3,5,9-undecatrienyl-1-aldehyde of formula (3) with tetra-alkyl methylene diphosphonate under protection of inert gases and the presence of bases to obtain 1,4,6,10-tetra-double bond pentadec-carbon phosphonate of formula (4) under reaction conditions of ether solvent or dipolar aprotic solvent at temperature of 0~30° C. Its reaction sequence is described as follows.

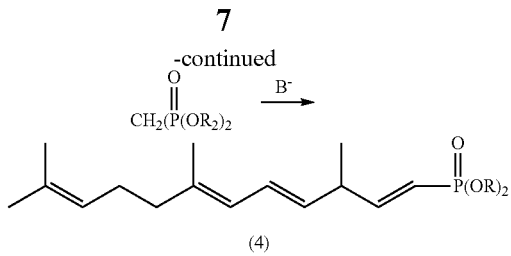

Wherein R is $C_{1-4}$ alkyl.

Preferably, a molar ratio of dosage of 2,6,10-trimethyl-3,5,9-undecatrienyl-1-aldehyde of formula (3) to the base is 1:1.0~1.2; a molar ratio of dosage of 2,6,10-trimethyl-3,5,9-undecatrienyl-1-aldehyde of formula (3) to tetra-alkyl methylene diphosphonate is 1:1.0~1.3.

More preferably, a molar ratio of dosage of 2,6,10-trimethyl-3,5,9-undecatrienyl-1-aldehyde of formula (3) to the base is 1:1.02~1.1; a molar ratio of dosage of 2,6,10-trimethyl-3,5,9-undecatrienyl-1-aldehyde of formula (3) to tetra-alkyl methylene diphosphonate is 1:1.05~1.15.

Preferably, the base is alkali metal hydride, alkali metal salt of alcohols or alkyl lithium; wherein the alkali metal hydride is sodium hydride or potassium hydride; the alkali metal salt of alcohols is sodium ethylate, sodium tert-butoxide or potassium tert-butoxide; the lithium alkyl is butyl lithium.

Preferably, the ether solvent is ether, tetrahydrofuran or ethylene glycol dimethyl ether; the dipolar aprotic solvent is dimethyl formamide, dimethyl sulfoxide, or hexamethyl phosphoric triamide.

Preferably, the Wittig-Horner condensation reaction proceeds at temperature of 10~20° C.

Preferably, the step (2) comprises reacting tetra-alkyl methylene diphosphonate with the base to produce a corresponding carbanion, and then proceeding a Wittig-Horner condensation reaction with 2,6,10-trimethyl-3,5,9-undecatrienyl-1-aldehyde of formula (3) added; or mixing tetra-alkyl methylene diphosphonate with 2,6,10-trimethyl-3,5,9-undecatrienyl-1-aldehyde of formula (3), and then slowly dropping it into the base.

C-14 aldehyde of formula (3) is prepared by using pseudoionone of formula (2) as raw materials (namely, 2,6,10-trimethyl-3,5,9-undecatrienyl-1-aldehyde), and then C-14 aldehyde of formula (3) proceeds a Wittig-Horner reaction condensation with tetra-alkyl methylene diphosphonate to obtain the objective compound 1,4,6,10-tetra-double bond pentadec-carbon phosphonate of formula (4). All of reactions proceed under protection of inert gas such as nitrogen, argon or one or more other inert gases.

In the method, the C-14 aldehyde of formula (3) is prepared by using pseudoionone of formula (2) according to methods of U.S. Pat. No. 4,000,131, that is, pseudoionone of formula (2) reacts with sulfonium salt to obtain epoxide of formula (9), and then to obtain C-14 aldehyde of formula (3) by catalyzing and opening ring.

As described above, it takes three steps for the present invention to produce the objective product of 1,4,6,10-tetra-double bond pentadec-carbon phosphonate of formula (4) by using pseudoionone as raw materials. The process route is simple. In the meantime both of raw materials pseudoionone and tetra-alkyl methylene diphosphonate are regular industrial raw materials, wherein such raw materials as tetra methyl methylene diphosphonate, tetra isopropyl methylene diphosphonate can commercially be obtained by Zhejiang Medicine Co. Ltd., Xinchang Pharmaceutical Factory). Hence raw materials of the present invention are easy to acquire, low cost and high industrial value.

The third objective of the present invention is to provide a method of preparing lycopene of formula (1) by using 1,4,6,10-tetra-double bond pentadec-carbon phosphonate of formula (4). The method comprises the following steps:

Step (1): proceeding a rearrangement reaction and dissociation of 1,4,6,10-tetra-double bond pentadec-carbon phosphonate of formula (4) under protection of inert gas and the presence of base, at temperature of −40~30° C. and in ether solvent or dipolar aprotic solvent;

Step (2): adding decyl di-aldehyde of formula (8) and proceeding a Wittig-Horner condensation reaction to prepare lycopene of formula (1) in the presence of bases, and under reaction conditions of ether solvent or dipolar aprotic solvent and at temperature of −40~30° C. Its reaction sequence is described as follows.

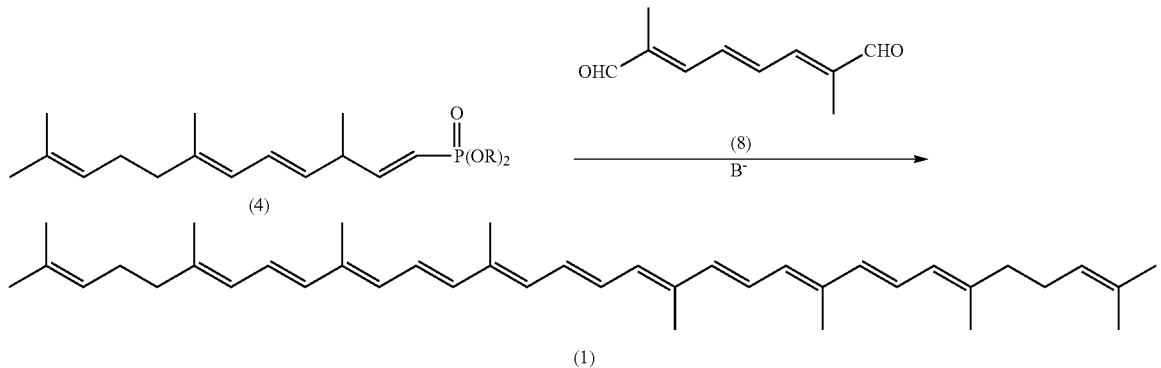

Preferably, a molar ratio of dosage of 1,4,6,10-tetra-double bond pentadec-carbon phosphonate of formula (4) to the base is 1:1.0~1.2; a molar ratio of dosage of 1,4,6,10-tetra-double bond pentadec-carbon phosphonate of formula (4) to decyl di-aldehyde of formula (8) is 1:0.4~0.6.

Preferably, the base is alkali metal salt of alcohols or lithium alkyl; wherein the alkali metal salt of alcohols is sodium ethylate, sodium tert-butoxide or potassium tert-butoxide; the lithium alkyl is butyl lithium.

Preferably, the ether solvent is ethyl ether, tetrahydrofuran or ethylene glycol di-methyl ether; the dipolar aprotic solvent is di-methyl formamide, dimethyl sulfoxide or hexa-methyl phosphoric triamide.

Preferably, both of the rearrangement reaction and the Wittig-Horner condensation reaction proceed at temperature of −20~10□.

Wherein decyl di-aldehyde of formula (8) is prepared by using the method disclosed in Example XIV of U.S. Pat. No. 5,061,819.

In above mentioned rearrangement and condensation reactions, 1,4,6,10-tetra-double bond pentadec-carbon phosphonate of formula (4) firstly reacts with the base to produce a corresponding carbanion, and then decyl di-aldehyde of formula (8) as raw materials of reaction is added to proceed a condensation reaction. It would be advantageous for fully rearrangement and dissociation of 1,4,6,10-tetra-double bond pentadec-carbon phosphonate of formula (4) as raw materials to produce carbanion, and it also would be better to control the Wittig-Horner condensation reaction.

As described above, it takes four steps for the present invention to produce the objective product of lycopene of formula (1) by using pseudoionone as raw materials, that is, 1,4,6,10-tetra-double bond pentadec-carbon phosphonate of formula (4) directly reacts and produces the objective product of lycopene of formula (1). Hence it takes the advantages of short process route. In the meantime these raw materials are easily obtained, low cost and high industrial value.

It is very easy to prepare 1,4,6,10-tetra-double bond pentadec-carbon phosphonate of formula (4) by the method of the present invention, and overcomes the deficiencies to difficultly handle the reduction technology of propadiene pentadec-carbon phosphonate being selectively reduced to 2,4,6,10-tetra-double bond pentadec-carbon phosphonate of formula (5).

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention.

Apparatuses and devices of Examples of the present invention are as follows: Gas chromatograph-Mass Spectrometer, MS5973N-GC6890N (Agilent Technologies, US); Nuclear Magnetic Resonance Spectrometer, AVANCE DMX □□400M (TMS as internal standard, Bruker Corporation); infrared spectrometer, NICOLET 360FT-IR; gas chromatograph, Techcomp Corp. 7890F.

Example 1

Preparation of
2,6,10-trimethyl-3,5,9-undecatrienyl-1-aldehyde of Formula (3)

20 g (0.5 ml) of sodium hydride (60% content) is added in 500 ml of three necked bottle under protection of nitrogen, and wash with 50 ml of n-hexane for twice per time to move out of paraffin oil from sodium hydride, and then 160 ml of DMSO is added. The mixture reacts 1 hour under stiffing and heating to 65° C. in an oil bath. The mixture emits large amounts of gas; and the mixture is cooled to room temperature after no gas comes out of it.

102 g (0.5 mol) of tri-methyl sulfonium salt iodide and 300 ml of a mixed solution of dimethyl sulfoxide and tetrahydrofuran with ratio of volume 1:1 are added in 1000 ml of another three necked bottle under protection of nitrogen and stiffing, and then cooled in a salt-ice bath, the sodium salt solution prepared is dropped into the three necked bottle at temperature of 0-5□ for half hour, and after continuously stirring for 20 minutes, 50 ml of tetrahydrofuran dissolving 38.4 g (0.2 mol) of pseudoionone of formula (2) is added into the three necked bottle kept at temperature of 0-5□ for half hour, and after continuously stirring for 2 hours, 20 ml of water is added after being finished, and stirring for 10 minutes, and then 200 of ml n-pentane and 200 ml of 10% NaCl solution are added, and layered, the organic layer is washed by 50 ml of 10% NaCl solution, and then dried by magnesium sulfate, filtered, solvent is evaporated under reduced pressure to dryness to obtain 35.2 g of crude product of epoxide of formula (9).

Magnesium bromide suspension is prepared by adding 7.6 g (0.04 mol) of 1,2-dibromoethane and 1.1 g (0.045 mol) of magnesium powder to 50 ml of ether, and 100 ml of ether dissolving 34.8 g of epoxide of formula (9) is dropped to the suspension at temperature of −10° C. of cold bath under stirring and protection of nitrogen for 20 minutes, after continuously stiffing for 5 minutes, 200 ml of ether is added to dilute this reaction solution. 200 ml of 10% NaCl solution is added and layered, the organic layer is washed by 50 ml of 10% NaCl solution, and then dried by magnesium sulfate, filtered, solvent is evaporated under reduced pressure to dryness to obtain 30.2 g of crude product of C-14 aldehyde of formula (3). The crude product comprises various isomer of 2R and 2S, 3-cis/trans and 5-cis/trans etc. Content of the crude product is 92.5% by GC analysis, the yield is 73.3%.

Determination of Product Structure:

GC-MS (m/e): 206, 191, 163, 135, 121, 109, 95 (100%), 69, 55, 41;

IR (v/cm$^{-1}$): 1672, 1612;

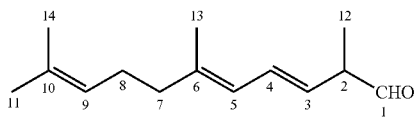

$^1$HNMR (δ ppm, 400 MHz, CDCl$_3$): 1.189-1.206 (m, 3H, C$_{12}$—H), 1.427 (s, 3H, C$_{14}$—H), 1.610 (s, 3H, C$_{11}$—H), 1.687 (s, 3H, C$_{13}$—H), 1.746-1.869 (m, 2H, C$_8$—H), 2.092-2.134 (m, 2H, C$_7$—H), 3.455-3.563 (m, 1H, C$_2$—H), 5.092-5.101 (m, 1H, C$_9$—H), 5.095-5.164 (m, 1H, C$_3$—H), 6.058 (d, J=9.6 Hz, 1H, C$_5$—H), 6.445 (t, J=9.6 Hz, 1H, C$_4$—H), 9.537 (s, 1H, —CHO);

$^{13}$CNMR (400 MHz, CDCl$_3$) δ (ppm): 201.03 (C1); 142.10 (C6); 128.56 (C4); 124.04 (C3); 123.75 (C9); 123.60 (C10); 119.34 (C5); 45.92 (C2); 40.27 (C7); 26.90 (C8); 25.66 (C11); 17.69 (C14); 16.67 (C13); 14.04 (C12);

DEPT135: 201.03; 128.56; 124.04; 123.75; 119.34; 45.92; 40.27 (D); 26.90 (D); 25.66; 17.69; 16.67; 14.04;

Example 2

Preparation of
3,7,11-trimethyl-1,4,6,10-dodecatetraenyl Phosphoric Acid Diethyl Ester 4.4 g (0.11 mol) of sodium hydride (60% content) is added in 250 ml of a three necked bottle under protection of nitrogen, and washed with 50 ml of n-hexane for twice per time to move out of paraffin oil from sodium hydride, and then 20 ml of toluene is added, 60 ml of toluene dissolving 34.5 g (0.12 mol) of tetra-ethyl methylene diphosphonate is dropped into this three necked bottle at temperature of 10-15□ of cold water bath with stiffing for half hour and emits a large amount of gas, continuously stirring for half hour. 40 ml of toluene dissolving 20.6 g of C-14 aldehyde of formula (3) (prepared by Example 1, 0.1 mol) is dropped at temperature of 10-15☐ of a cold water bath for half hour, continuously stiffing for half hour. 80 ml of water is added to this reaction solution and stirring for 10 minutes, layered, the organic layer is washed by 50 ml of 10% NaCl solution, and then dried by magnesium sulfate, filtered; solvent is evaporated with reduced pressure and then reacts at temperature of 20-25° C. for one hour. 100 ml of chloroform is added after reaction finished, and washed with 5% NaCl solution (75 ml every time) for three times, the organic layer is dried by magnesium sulfate and filtered, the filtrate is evaporated with reduced pressure to move out of solvent to obtain crude product of lycopene, 3.3 g of lycopene is obtained by recrystallization of 30 ml of di-chloro methane, the yield of lycopene is 61.6%.

Determination of Product Structure:

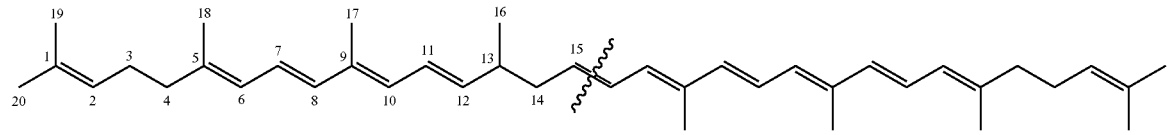

to dryness to obtain 30.2 g of crude product of 3,7,11-trimethyl-1,4,6,10-dodecatetraenyl phosphoric acid diethyl ester, the product is light brown liquid, content of gas phase is 93.2%, the yield is 88.8%.

Determination of Product Structure:

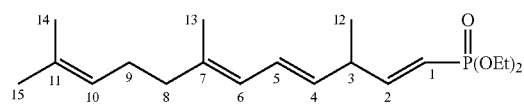

$^1$HNMR (δ ppm, 400 MHz, CDCl$_3$): 6.741 (t, J=19.6 Hz, 1H, C2-H), 6.242 (t, J=11.2 Hz, 1H, C5-H), 5.996 (d, J=11.6 Hz, 1H, C6-H), 5.628 (t, J=19.2 Hz, 1H, C$_1$—H), 5.062-5.141 (m, 2H, C4-H and C10-H), 4.023-4.095 (m, 4H, O—C*H$_2$—CH$_3$), 3.43-3.53 (m, 1H, C3-H), 2.056-2.151 (m, 4H, C8-H and C9-H), 1.825 and 1.803 (s, 3H, C13-H), 1.686 (s, 3H, C14-H), 1.609 (s, 3H, C15-H), 1.313 (t, J=7.2 Hz, 6H, O—CH2-C*H3), 1.154 (d, J=6.8 Hz, 3H, C12-H)

$^{13}$CNMR (400 MHz, CDCl$_3$) δ (ppm): 156.69 (C2); 140.61 (C7); 131.73 (C11); 129.91 (C4); 125.49 (C6); 123.86 (C10); 119.36 (C5); 115.79 and 113.93 (C1); 61.62, 61.57 (O—C*H2-CH3); 40.25 (C8); 36.19 and 35.98 (C3); 26.57 (C9); 25.67 (C15); 19.72 (C13); 17.67 and 17.62 (C12); 16.87 (C14); 16.34 and 16.28 (O—CH$_2$—C*H$_3$)

DEPT135: 156.69; 129.91; 125.49; 123.86; 119.36; 115.79 and 113.93; 61.62 (D), 61.57 (D); 40.25 (D); 36.19 and 35.98; 26.57 (D); 25.67; 19.72; 17.67 and 17.62; 16.87; 16.34 and 16.28

Example 3

Preparation of Lycopene from 3,7,11-trimethyl-1,4,6,10-dodecatetraenyl Phosphoric Acid Di-Ethyl Ester 6.8 g (0.02 mol) of 3,7,11-trimethyl-1,4,6,10-dodecatetraenyl phosphoric acid di-ethyl ester prepared by Example 2 and 30 ml of mixed solution of tetrahydrofuran and dimethyl sulfoxide with ratio of volume 8:1 are added into 250 ml of a three necked bottle under protection of nitrogen, 2.3 g (0.021 mol) of potassium tert-butoxide is added at 5° C. of ice-water bath and stirring, continuously stiffing at the same temperature for two hours, and then 10 ml of tetrahydrofuran and dimethyl sulfoxide (a ratio of volume of tetrahydrofuran to dimethyl sulfoxide is 8:1) dissolving 1.6 g (0.0098 mol) of decyl di-aldehyde of formula (8) is dropped for 20 minutes, continuously stiffing at the same temperature for 15 minutes, $^1$HNMR (δ ppm, 400 MHz, CDCl$_3$): δ 5.111, 5.975-6.943 (m, 8H, double bond H), 5.11 (m, 1H), 1.552 (S, 6H), 1.616 (S, 3H), 1.689 (S, 3H), 2.129 (S, 3H), 1.427-2.212 (m, 4H)

$^{13}$CNMR (400 MHz, CDCl$_3$) δ (ppm): 139.52 (C5); 137.37 (C12); 136.56 (C13); 136.19 (C9); 135.42 (C10); 132.66 (C14); 131.76 (C1); 131.58 (C8); 130.09 (C15); 125.73 (C11); 125.17 (C2); 124.82 (C6); 123.96 (C7); 40.25 (C4); 26.69 (C3); 25.72 (C20); 18.42 (C19); 16.97 (C18); 12.91 (C17); 12.81 (C16)

There are 13 peaks between δ (ppm) 120 and 140; 7 peaks between δ (ppm) 10 and 45, which determine all trans-structure and high purification of the product.

DEPT135: 137.37; 135.42; 132.66; 131.58; 130.09; 125.73; 125.17; 124.82; 123.96; 58.48 (D); 40.25 (D); 26.69 (D); 25.72; 18.42; 16.97; 12.91; 12.81

Example 4

Preparation of 3,7,11-trimethyl-1,4,6,10-dodecatetraenyl Phosphoric Acid Dimethyl Ester 0.88 g (0.022 ml) of sodium hydride (60% content) is added in 100 ml of three necked bottle under protection of nitrogen, and washed with 8 ml of n-hexane for twice per time to move out of paraffin oil from sodium hydride, and then 10 ml of toluene is added, 20 ml of toluene dissolving 5.6 g (0.024 mol) of tetra-methyl methylene diphosphonate is dropped into this three necked bottle at temperature of 10-15° C. of cold water bath and stiffing for half hour and emits a large amount of gas, continuously stirring for 20 minutes. 15 ml of toluene dissolving 4.1 g of C-14 aldehyde of formula (3) (prepared by Example 1, 0.02 mol) is dropped at temperature of 10-15° C. of cold water bath for half hour, continuously stirring for 20 minutes. 20 ml of water is added to this reaction solution under stiffing for 10 minutes, layered, the organic layer is washed by 20 ml 10% NaCl solution, and then dried by magnesium sulfate, filtered; solvent is evaporated with reduced pressure to dryness to obtain 6.2 g of crude product of 3,7,11-trimethyl-1,4,6,10-dodecatetraenyl phosphoric acid di-methyl ester, the product is light brown liquid, content of gas phase is 92.6%, the yield of product is 92.0%.

Determination of Product Structure:

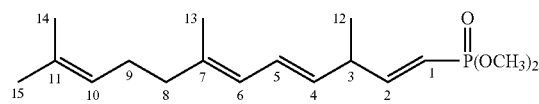

1HNMR (δ ppm, 400 MHz, CDCl$_3$): 6.782 (t, J=19.6 Hz, 1H, C2-H), 6.255 (t, J=11.2 Hz, 1H, C5-H), 5.995 (d, J=11.6 Hz, 1H, C6-H), 5.603 (t, J=19.2 Hz, 1H, C$_1$—H), 5.057-5.138 (m, 2H, C4-H and C10-H), 3.712 (d, J=11.2 Hz, O—C*H3), 3.450-3.550 (m, 1H, C3-H), 2.056-2.151 (m, 4H, C8-H and C9-H), 1.809 and 1.773 (s, 3H, C13-H), 1.688 (s, 3H, C14-H), 1.612 (s, 3H, C15-H), 1.162 (d, J=6.8 Hz, 3H, C12-H)

Example 5

Preparation of 3,7,11-Trimethyl-1,4,6,10-Dodecatetraenyl Phosphoric Acid Di-Isopropyl Ester 0.88 g (0.022 ml) of sodium hydride (60% content) is added in 100 ml of three necked bottle under protection of nitrogen, and washed with 8 ml of n-hexane for twice per time to move out of paraffin oil from sodium hydride, and then 10 ml of toluene is added, 20 ml of toluene dissolving 8.26 g (0.024 mol) of tetra-isopropyl methylene diphosphonate is dropped into this three necked bottle at temperature of 10-15° C. of cold water bath and stiffing for half hour and emits a large amount of gas, continuously stirring for 20 minutes. 15 ml of toluene dissolving 4.1 g of C-14 aldehyde of formula (3) (prepared by Example 1, 0.02 mol) is dropped at temperature of 10-15° C. of cold water bath for half hour, continuously stiffing for 20 minutes. 20 ml of water is added to the reaction solution under stiffing for 10 minutes, layered, the organic layer is washed with 20 ml of 10% NaCl solution, and then dried by magnesium sulfate, filtered; solvent is evaporated with reduced pressure to dryness to obtain 7.1 g of crude product of 3,7,11-trimethyl-1,4,6,10-dodecatetraenyl phosphoric acid di-isopropyl ester, the product is light brown liquid, content of gas phase is 93.1%, the yield is 89.8%.
Determination of Product Structure:

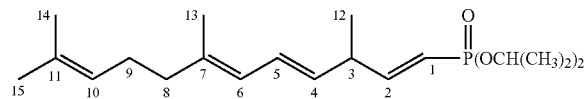

$^1$HNMR (δ ppm, 400 MHz, CDCl$_3$): 6.720 (t, J=19.6 Hz, 1H, C2-H), 6.246 (t, J=11.2 Hz, 1H, C5-H), 6.002 (d, J=11.6 Hz, 1H, C6-H), 5.639 (t, J=18.8 Hz, 1H, C$_1$—H), 5.067-5.147 (m, 2H, C4-H and C10-H), 4.601-4.698 (m, 2H, O—C*H), 3.482-3.503 (m, 1H, C3-H), 2.056-2.151 (m, 4H, C8-H and C9-H), 1.804 (s, 3H, C13-H), 1.695 (s, 3H, C14-H), 1.618 (s, 3H, C15-H), 1.352 (d, J=6.0 Hz, 12H, CH—(C*H3)2), 1.269 (d, J=6.0 Hz, 3H, C12-H)

Example 6

Preparation of Lycopene from 3,7,11-Trimethyl-1,4,6,10-Dodecatetraenyl Phosphoric Acid Di-Methyl Ester 6.0 g (0.018 mol) of 3,7,11-trimethyl-1,4,6,10-dodecatetraenyl phosphoric acid di-methyl ester prepared by Example 4 and 30 ml of tetrahydrofuran and dimethyl sulfoxide (a ratio of volume of tetrahydrofuran to dimethyl sulfoxide is 8:1) are added into 100 ml of three necked bottle under protection of nitrogen, 2.0 g (0.018 mol) of potassium tert-butoxide is added at temperature of 5° C. of ice-water bath under stiffing, continuously stiffing at the same temperature for two hours, and then 10 ml of tetrahydrofuran and dimethyl sulfoxide (a ratio of volume of tetrahydrofuran to dimethyl sulfoxide is 8:1) dissolving 1.5 g (0.0092 mol) of decyl di-aldehyde of formula (8) of is dropped for 20 minutes, continuously stiffing at the same temperature for 15 minutes, and then reacts at temperature of 20-25° C. for one hour. 100 ml of chloroform is added after reaction finished, and washed with 5% NaCl solution (75 ml every time) for three times, the organic layer is dried by magnesium sulfate and filtered, the filtrate is evaporated with reduced pressure to move out of solvent to obtain crude product of lycopene, 2.8 g of lycopene is obtained by recrystallization of 30 ml of di-chloro methane with the yield of 58.1%. $^1$H NMR of the product (lycopene) is consistent with that of product of Example 3.

Example 7

Preparation of Lycopene from 3,7,11-Trimethyl-1,4,6,10-Dodecatetraenyl Phosphoric Acid Di-Isopropyl Ester 7.1 g (0.018 mol) of 3,7,11-trimethyl-1,4,6,10-dodecatetraenyl phosphoric acid di-isopropyl ester prepared by Example 5 and 30 ml of tetrahydrofuran and dimethyl sulfoxide (a ratio of volume of tetrahydrofuran to dimethyl sulfoxide is 8:1) are added into 100 ml of three necked bottle under protection of nitrogen, 2.0 g (0.018 mol) of potassium tert-butoxide is added at temperature of 5° C. of ice-water bath under stiffing, continuously stiffing at the same temperature for two hours, and then 10 ml of tetrahydrofuran and dimethyl sulfoxide (a ratio of volume of tetrahydrofuran to dimethyl sulfoxide is 8:1) dissolving 1.5 g (0.0092 mol) of decyl di-aldehyde of formula (8) of is dropped for 20 minutes, continuously stirring at the same temperature for 15 minutes, and then reacts at temperature of 20-25□ for one hour. 100 ml of chloroform is added after reaction finished, and washed with 5% NaCl solution (75 ml every time) for three times, the organic layer is dried by magnesium sulfate and filtered, the filtrate is evaporated with reduced pressure to move out of solvent to obtain crude product of lycopene, 2.9 g of lycopene of product is obtained by recrystallization of 30 ml of di-chloro methane with yield of 60.2%. $^1$H NMR of product is consistent with that of product of lycopene of Example 3.

Example 8

Preparation of 2,6,10-trimethyl-3,5,9-undecatrienyl-1-aldehyde of Formula (3)

C-14 aldehyde of formula (3) prepared by the process of Example 1, 31.3 g of crude product is obtained, which contains various isomer of 2R and 2S, 3-cis/trans and 5-cis/trans etc. Content of product is 91.5% by GC analysis; the yield is 75.1%. $^1$H NMR of the product is consistent with that of the product of Example 1.

Example 9

Preparation of 3,7,11-trimethyl-1,4,6,10-dodecatetraenyl Phosphoric Acid Di-Ethyl Ester 1.76 g (0.022 ml) of potassium hydride (50% content) is added in 100 ml of three necked bottle under protection of nitrogen, and washed with 8 ml of n-hexane for twice per time to move out of paraffin oil from it, and then 10 ml of toluene is added, 20 ml of toluene dissolving 6.9 g (0.024 mol) of tetra-ethyl methylene diphosphonate is dropped into this three necked bottle at temperature of 10-15□ of cold water bath and stirring for half hour and emits a large amount of gas, continuously stirring for 20 minutes. 15 ml of toluene dissolving 4.1 g of C-14 aldehyde of formula (3) (prepared by Example 1, 0.02 mol) is dropped at temperature of 10-15□ of cold water bath for half hour, continuously stiffing for 20 minutes. 20 ml of water is added to the reaction solution under stirring for 10 minutes, layered, the organic layer is washed with 20 ml of 10% NaCl solution, and then dried by magnesium sulfate, filtered; solvent is evaporated to dryness with reduced pressure to obtain 6.4 g of crude product of 3,7,11-trimethyl-1,4,6,10-dodecatetraenyl phosphoric acid di-ethyl ester, the product is light brown liquid, content of gas phase is 92.8%, the yield is 93.1%. $^1$H NMR of the product is consistent with that of product of Example 2.

Example 10-15

Preparation of 3,7,11-Trimethyl-1,4,6,10-Dodecatetraenyl Phosphoric Acid Di-Ethyl Ester Under Conditions of Different Bases, Solvents and Temperatures Some amount of base and some kind of solvent are added in 100 ml of three necked bottle under protection of nitrogen (kind of base and solvent are shown in table 1), and then 10 ml of the solvent (the same as the above mentioned solvent) dissolving some amount of tetra-ethyl methylene diphosphonate (a molar weight is shown in Table 1) is dropped into this three necked bottle at temperature of 10-15□ of cold water bath under stiffing for half hour and emits gas, continuously stiffing for 20 minutes. 10 ml of the solvent (the same as the above mentioned solvent) dissolving 2.1 g of C-14 aldehyde of formula (3) (prepared by Example 8, 0.010 mol) is dropped under a temperature of cold water bath for half hour, continuously stiffing for 20 minutes at the same temperature. 10 ml of water and 20 ml of ether are added to the reaction solution under stirring for 10 minutes, layered, the organic layer is washed by 20 ml of 10% NaCl solution, and then dried by magnesium sulfate, filtered; solvent is evaporated to dryness with reduced pressure to obtain crude product of 3,7,11-trimethyl-1,4,6,10-dodecatetraenyl phosphoric acid di-ethyl ester, the product is light brown liquid, measuring content of gas phase, and calculating yield, the result is shown in Table 1.

TABLE 1

Table 1: Using different base and different solvent to replace Sodium hydride and toluene, and adjusting dosage of base, the result is shown in Table 1:
(Note: alkoxy Alkali metal is namely methoxy sodium or ethoxy sodium; butyl lithium is 2.5 mol/l n-hexane solution thereof)

| Example | Base | Dosage of base (molar) | Solvent | Methylene bisphosphonic acid tetra-ethyl ester (molar) | Temperature of reaction (° C.) | Amount (g) content (%) of product | yield (%) |
|---|---|---|---|---|---|---|---|
| 10 | ethoxy sodium | 0.0120 | toluene | 0.0130 | 5 | 3.0; 93.2 | 87.7 |
| 11 | sodium tert-butoxide | 0.0100 | ethylene glycol dimethyl ether | 0.0100 | 10 | 3.1; 92.9 | 84.7 |
| 12 | potassium tert-butoxide | 0.0102 | dimethyl formamide | 0.0105 | 20 | 3.2; 93.1 | 87.6 |
| 13 | n-butyl lithium | 0.0120 | tetrahydrofuran/n-hexane | 0.0130 | 0 | 3.3; 93.5 | 90.8 |
| 14 | DMSO sodium salt | 0.0105 | DMSO | 0.0108 | 30 | 2.9; 91.3 | 77.9 |
| 15 | methoxy sodium | 0.0110 | ether | 0.0115 | 15 | 1.9; 89.7 | 50.1 |

Note:
n-butyl lithium is 2.5 mol/l n-hexane solution thereof
Products of Example 10-15 are determined by nuclear magnetic structure, 1H NMR thereof is consistent with that of product of Example 2.

Example 16

Preparation of 3,7,11-Trimethyl-1,4,6,10-Dodecatetraenyl Phosphoric Acid Di-Ethyl Ester 0.88 g (0.022 ml) of sodium hydride (60% content) is added in 100 ml of three necked bottle under protection of nitrogen, and washed with 8 ml of n-hexane for twice per time to move out of paraffin oil from sodium hydride, and then 10 ml of toluene is added, 40 ml of toluene dissolving 6.9 g (0.024 mol) of tetra-ethyl methylene diphosphonate and 4.1 g of C-14 aldehyde of formula (3) (prepared by Example 8, 0.02 mol) is dropped into this three necked bottle at temperature of 10-15° C. of cold water bath under stirring for half hour and emits a large amount of gas, continuously stiffing for 20 minutes. 20 ml of water is added to the reaction solution, stirring for 10 minutes, layered, the organic layer is washed with 20 ml of 10% NaCl solution, and then dried by magnesium sulfate, filtered; solvent is evaporated to dryness with reduced pressure to obtain 6.7 g of crude product of 3,7,11-trimethyl-1,4,6,10-dodecatetraenyl phosphoric acid di-ethyl ester, the product is light brown liquid, content of gas phase is 92.3%, the yield is 93.1%. $^1$H NMR of the product is consistent with that of product of Example 2.

Example 17-21

Preparation of Lycopene from 3,7,11-Trimethyl-1,4,6,10-Dodecatetraenyl Phosphoric Acid Di-Ethyl Ester Under Conditions of Different Bases, Solvents and Temperatures Combine products of 3,7,11-trimethyl-1,4,6,10-dodecatetraenyl phosphoric acid di-ethyl ester prepared by Examples 9~16 to obtain 30.5 g of crude product with content of 92.6%, which is used for preparing lycopene hereafter, and use different bases, solvents, and different temperatures to do series of experiment. The process is described as follows.

3.4 g (0.01 mol) of crude product of 3,7,11-trimethyl-1,4,6,10-dodecatetraenyl phosphoric acid di-ethyl ester and 20 ml of some kind of solvent are added into 100 ml of three necked bottle under protection of nitrogen, certain amount of base is added at a certain temperature (kind of base and solvent is shown in Table 2) under stiffing, continuously stiffing for two hours, and then 10 ml of the solvent (the same as solvent described above) dissolving certain amount of decyl di-aldehyde of formula (8) is dropped during 20 minutes at a certain temperature (the same as the temperature of rearrangement and dissociation described above), continuously stirring at the same temperature for 15 minutes, and then reacts at temperature of 25-30□ for one hour. 100 ml of chloroform is added after reaction finished, and washed with 5% NaCl solution (75 ml every time) for three times, the organic layer is dried by magnesium sulfate and filtered, the filtrate is evaporated with reduced pressure to move out of solvent to obtain crude product of lycopene, certain amount of lycopene of product is obtained by recrystallization of 30 ml of di-chloro methane, calculating yield, the result is shown in Table 2.

best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. 1,4,6,10-tetra-double bond pentadec-carbon phosphonate of formula (4), the 1,4,6,10-tetra-double bond pentadec-carbon phosphonate is 3,7,11-trimethyl-1,4,6,10-dodecatetraenyl phosphoric acid dialkyl ester.

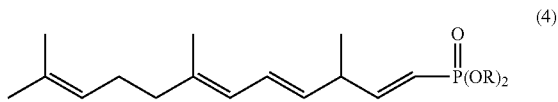

(4)

wherein R is $C_{1-4}$ alkyl.

2. 1,4,6,10-pentadecatetraenyl phosphonic acid ester according to claim 1, wherein the 1,4,6,10-tetra-double bond pentadec-carbon phosphonate is 3,7,11-trimethyl-1,4,6,10-dodecatetraenyl phosphoric acid di-methyl ester, 3,7,11-trimethyl-1,4,6,10-dodecatetraenyl phosphoric acid di-ethyl ester, 3,7,11-trimethyl-1,4,6,10-dodecatetraenyl phosphoric acid di-isopropyl ester.

TABLE 2

Table 2: Process of preparation is the same as that of example 4; the difference is only using different base and solvent and different temperature, adjusting usage of base and decyl di-aldehyde, the result is shown in Table 2:

| Example | Base | Dosage of base (molar) | Solvent | Methylene bisphosphonic acid tetra-ethyl ester (molar) | Temperature of reaction (° C.) | Amount(g) content (%) of product | yield (%) |
|---|---|---|---|---|---|---|---|
| 17 | ethoxy Sodium | 0.0120 | Ethyl ether | 0.006 | −5 | 1.1 | 41.1 |
| 18 | sodium tert-butoxide | 0.0102 | ethylene glycol dimethyl ether | 0.005 | 10 | 1.5 | 56.1 |
| 19 | potassium tert-butoxide | 0.0105 | dimethyl formamide | 0.0045 | −20 | 1.7 | 63.5 |
| 20 | potassium tert-butoxide | 0.0105 | hexa-methyl phosphoric triamide. | 0.0040 | −30 | 1.6 | 59.8 |
| 21 | n-butyl lithium | 0.0110 | tetrahydrofuran/ n-hexane | 0.0055 | −40 | 1.9 | 71.0 |

Note:
n-butyl lithium is 2.5 mol/l n-hexane solution thereof
Products of Examples 17-21 are determined by nuclear magnetic structure, 1H NMR thereof is consistent with that of product of Example 3.

Although the present invention has been described in connection with the above embodiments, it should be understood that the present invention is not limited to such preferred embodiments and procedures set forth above. The embodiments and procedures were chosen and described in order to 3. A method of preparing the 1,4,6,10-tetra-double bond pentadec-carbon phosphonate of formula (4), the method comprises the following steps:

Step (1): reacting a pseudo ionone of formula (2) with sulfonium salt under protection of inert gases to prepare a epoxide of formula (9), and then reacting the epoxide of formula (9) with magnesium bromide to prepare 2,6,10-trimethyl-3,5,9-undecatrienyl-1-aldehyde; its reaction sequence is described as follows:

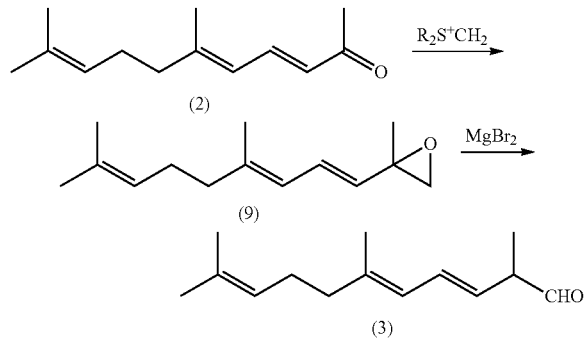

Step (2): reacting a 2,6,10-trimethyl-3,5,9-undecatrienyl-1-aldehyde of formula (3) with tetra-alkyl methylene diphosphonate (i) in the presence of inert gases and bases and (ii) in an ether or dipolar aprotic solvent at temperature of 0-30° C. in a Wittig Horner condensation reaction; its reaction sequence is described as follows:

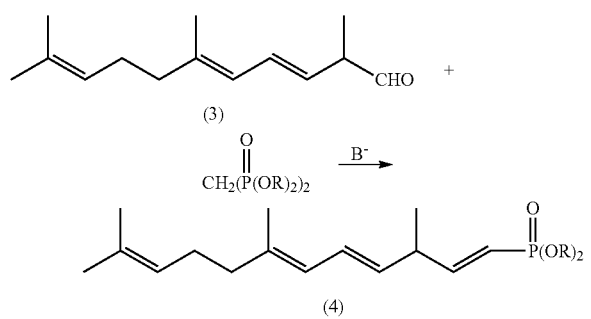

wherein R is $C_{1-4}$ alkyl.

4. The method according to claim 3, wherein a molar ratio of dosage of 2,6,10-trimethyl-3,5,9-undecatrienyl-1-aldehyde of formula (3) to the base is 1:1.0~1.2; a molar ratio of dosage of 2,6,10-trimethyl-3,5,9-undecatrienyl-1-aldehyde of formula (3) to tetra-alkyl methylene diphosphonate is 1:1.0~1.3.

5. The method according to claim 4, wherein a molar ratio of dosage of 2,6,10-trimethyl-3,5,9-undecatrienyl-1-aldehyde of formula (3) to the base is 1:1.02~1.1; a molar ratio of dosage of 2,6,10-trimethyl-3,5,9-undecatrienyl-1-aldehyde of formula (3) to tetra-alkyl methylene diphosphonate is 1:1.05~1.15.

6. The method according to claim 5, wherein the base is alkali metal hydride, alkali metal salt of alcohols or lithium alkyl; wherein the alkali metal hydride is sodium hydride or potassium hydride; the alkali metal salt of alcohols is sodium ethylate, sodium tert-butoxide or potassium tert-butoxide; the lithium alkyl is butyl lithium.

7. The method according to claim 3, wherein the ether solvent is ether, tetrahydrofuran or ethylene glycol dimethyl ether; the dipolar aprotic solvent is dimethyl formamide, dimethyl sulfoxide or hexamethyl phosphoric triamide.

8. The method according to claim 3, wherein the Wittig-Horner condensation reaction proceeds at temperature of 10-20° C.

9. The method according to claim 3, wherein the step (2) comprises reacting tetra-alkyl methylene diphosphonate with the base to produce a corresponding carbanion, and then proceeding a Wittig-Horner condensation reaction with 2,6,10-trimethyl-3,5,9-undecatrienyl-1-aldehyde of formula (3) added; or mixing tetra-alkyl methylene diphosphonate with 2,6,10-trimethyl-3,5,9-undecatrienyl-1-aldehyde of formula (3), and then slowly dropping it into the base.

10. A method of preparing lycopene of formula (1) by using 1,4,6,10-tetra-double bond pentadec-carbon phosphonate of formula (4), the method comprising the following steps:
Step (1): adding decyl di-aldehyde of formula (8) for a rearrangement reaction and dissociation of 1,4,6,10-tetra-double bond pentadec-carbon phosphonate of formula (4) under protection of inert gas and the presence of base, at temperature of −40~30° C. and in ether solvent or dipolar aprotic solvent;
Step (2): conducting a Wittig-Horner condensation reaction to prepare lycopene of formula (1) in the presence of bases, and under reaction conditions of ether solvent or dipolar aprotic solvent and at temperature of −40~30° C.; its reaction sequence is described as follows.

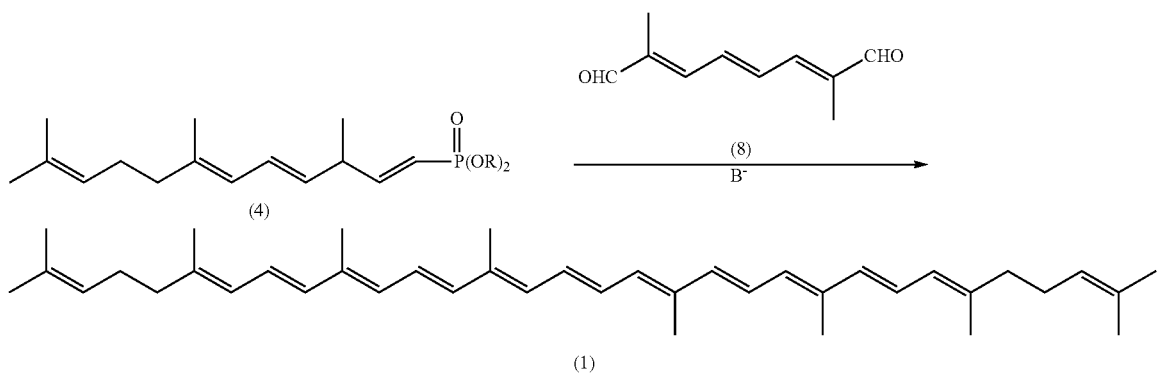

11. The method according to claim 10, wherein a molar ratio of dosage of 1,4,6,10-tetra-double bond pentadec-carbon phosphonate of formula (4) to the base is 1:1.0~1.2; a molar ratio of dosage of 1,4,6,10-tetra-double bond pentadec-carbon phosphonate of formula (4) to decyl di-aldehyde of formula (8) is 1:0.4~0.6.

12. The method according to claim 11, wherein the base is alkali metal salt of alcohols or lithium alkyl; wherein the alkali metal salt of alcohols is sodium ethylate, sodium tert-butoxide or potassium tert-butoxide; the lithium alkyl is butyl lithium.

13. The method according to claim 10, wherein the ether solvent is ethyl ether, tetrahydrofuran or ethylene glycol di-methyl ether; the dipolar aprotic solvent is di-methyl formamide, dimethyl sulfoxide or hexa-methyl phosphoric triamide.

14. The method according to claim 10, wherein both of the rearrangement reaction and the Wittig-Horner condensation reaction proceed at temperature of $-20 \sim 10°$ C.

* * * * *